(12) United States Patent
Johnson et al.

(10) Patent No.: US 11,666,472 B2
(45) Date of Patent: Jun. 6, 2023

(54) ANKLE ORTHOSIS

(71) Applicant: Icarus Medical, LLC, Charlottesville, VA (US)

(72) Inventors: David T. Johnson, Charlottesville, VA (US); Evan Eckersley, Charlottesville, VA (US); Ben Scire, Hopkinton, MA (US); Carter Kitchin, Charlottesville, VA (US)

(73) Assignee: Icarus Medical, LLC, Charlottesville, VA (US)

( * ) Notice: Subject to any disclaimer, the term of this patent is extended or adjusted under 35 U.S.C. 154(b) by 0 days.

(21) Appl. No.: 17/537,476

(22) Filed: Nov. 29, 2021

(65) Prior Publication Data

US 2022/0079794 A1   Mar. 17, 2022

Related U.S. Application Data

(60) Continuation-in-part of application No. 17/211,635, filed on Mar. 24, 2021, which is a continuation of
(Continued)

(51) Int. Cl.
*A61F 5/01* (2006.01)

(52) U.S. Cl.
CPC .... *A61F 5/0125* (2013.01); *A61F 2005/0139* (2013.01); *A61F 2005/0165* (2013.01)

(58) Field of Classification Search
CPC ............ A61F 5/0125; A61F 2005/0139; A61F 2005/0165; A61F 5/0113; A61F 5/0111; A61F 5/0585; A61B 5/4528; A61B 5/1121

See application file for complete search history.

(56) References Cited

U.S. PATENT DOCUMENTS

| | | | | |
|---|---|---|---|---|
| 4,934,355 A * | 6/1990 | Porcelli | ................. | A61F 5/0127 602/27 |
| 5,277,699 A * | 1/1994 | Williamson | .......... | A61F 5/0118 128/882 |
| 6,783,555 B2 * | 8/2004 | Kuhn | .................... | A61F 5/0102 482/66 |
| 7,678,067 B1 * | 3/2010 | Smith | ................... | A61F 5/0127 602/23 |
| 9,021,614 B2 | 5/2015 | Tepper et al. | | |

(Continued)

FOREIGN PATENT DOCUMENTS

| CA | 3000778 C | 3/2022 |
|---|---|---|
| EP | 3010456 B1 | 5/2020 |

*Primary Examiner* — Ophelia A Hawthorne
(74) *Attorney, Agent, or Firm* — Woods Rogers Vandeventer Black; Nathan Evans; Timothy J. Bechen

(57) ABSTRACT

A multi-axis rotation control ankle brace, wherein the direction and magnitude of force can be controlled around three axes of the ankle joint through an adjustable tensioning apparatus. The device may be applied to address conditions such as chronic ankle instability, foot drop, or osteoarthritis by providing such forces around the joint as an external-muscle tendon system to improve function, reduce pain, or restore mobility of the user. While more are contemplated herein, five preferred embodiments are specifically disclosed in the current application. Three preferred embodiments comprise a proximal portion and a distal portion, wherein the proximal portion is anchored above the ankle joint and houses, in aspects, the adjustment mechanism. The proximal portion is connected to the distal portion by tensioning or compressive elements, through which forces can be controlled by the user via the adjustment mechanism. In other preferred embodiments, the device is comprised of one continuous mesh, sock or sleeve through which tension can be controlled by the user. In other preferred embodiments, the device is personalized to the user through multiple aspects including user-enabled adjustment of forces around the joint. The device may be customized by 3D printing a device based on a digital scan, and therefore conforms to the user's ankle and foot.

23 Claims, 8 Drawing Sheets

Related U.S. Application Data application No. 17/074,542, filed on Oct. 19, 2020, which is a division of application No. 15/585,968, filed on May 3, 2017, now Pat. No. 10,806,619, said application No. 17/537,476 is a continuation-in-part of application No. 17/074,571, filed on Oct. 19, 2020, which is a continuation-in-part of application No. 15/585,968, filed on May 3, 2017, now Pat. No. 10,806,619, said application No. 17/537,476 is a continuation-in-part of application No. PCT/US2020/047904, filed on Aug. 26, 2020.

(60) Provisional application No. 62/331,315, filed on May 3, 2016.

(56) References Cited

U.S. PATENT DOCUMENTS

| | | | |
|---|---|---|---|
| 9,248,040 B2 | 2/2016 | Soderberg et al. | |
| 9,427,350 B1 | 8/2016 | Clements | |
| 9,707,118 B1* | 7/2017 | Meyer | A61F 5/0127 |
| 2008/0004558 A1* | 1/2008 | Outred | A61F 5/0113 |
| | | | 602/23 |
| 2011/0308110 A1 | 12/2011 | Berns et al. | |
| 2014/0257156 A1* | 9/2014 | Capra | A43C 11/165 |
| | | | 602/5 |
| 2015/0032041 A1 | 1/2015 | Ingimundarson et al. | |
| 2016/0135978 A1* | 5/2016 | McGovern | A61F 5/0127 |
| | | | 602/27 |
| 2018/0333285 A1 | 11/2018 | Thor et al. | |

* cited by examiner

ABSTRACT

ANKLE ORTHOSIS

CROSS-REFERENCE TO RELATED APPLICATIONS

The present application is a continuation-in-part of and relies on the disclosures of and claims priority to and the benefit of the filing dates of U.S. patent application Ser. Nos. 17/074,571 and 17/074,542 filed Oct. 19, 2020, U.S. patent application Ser. Nos. 17/211,590 and 17/211,635 filed Mar. 24, 2021, which rely on the disclosures of and claim priority to and the benefit of the filing date of U.S. patent application Ser. No. 15/585,968, filed May 3, 2017, which claims priority to and benefit from U.S. Provisional Patent Application No. 62/331,315 filed on May 3, 2016. This application also relates to and relies on the disclosures of and claims priority to and the benefit of the filing date of PCT/US2020/047904, filed Aug. 26, 2020. The disclosures of those applications are hereby incorporated by reference herein in their entirety.

BACKGROUND OF THE INVENTION

Field of the Invention

The present invention disclosed herein relates to an ankle orthosis comprising an adjustable tensioning apparatus designed to control rotation of the ankle joint around one or more axes.

Description of Related Art

The ankle presents one of the more complicated joints within the body, as well as one facing a diverse range of prevalent indications. Individuals may be affected by conditions ranging from ankle sprain to foot drop to osteoarthritis. Each condition may arise due to a range of underlying causes including a chronic condition from prior injury, a neurological disorder, or general musculoskeletal deficiencies. For example, 3.6% of the population experiences ankle sprains annually within the US. Most individuals experiencing ankle sprains pursue self-treatment options such as the PRICE method (protection, rest, ice, compression, and elevation). Immobilization in the form of bracing is often pursued. Due to self-treatment, sprains are largely underreported because most patients never visit a clinic or professional.

While this injury may seem temporary to the individual at the time of the sprain, it presents serious long-term implications. Such indications include chronic ankle instability (CAI) resulting in recurring sprains, tendon and ligament damage, osteoarthritis, and fracture. Most sprains (70%) involve a lateral sprain (inversion). While most ankle sprains are successfully managed with nonoperative modalities, recurrent instability and associated defects can be seen in 25-40% of patients, which only accounts for those reported in a largely unreported field. The incidence of residual symptoms following acute ankle sprain is variable, but has been reported with rates between 40-50%. Additionally, 40-70% of patients sustaining a lateral ankle sprain may develop CAL, characterized by residual symptoms of the ankle 'giving way' and feelings of ankle joint instability for at least one year following the initial sprain. The condition ultimately leads to insufficiency of the lateral ankle ligament complex. This negatively alters central mechanisms of motor control, leading to an increased risk of falls, and is a leading cause of post-traumatic ankle joint osteoarthritis. It also affects the user's gait and creates a compounding effect on biomechanics of other lower limb joints, including the knee, hip and back. Ultimately, a single sprain may result in a significantly reduced quality of life, which is associated with increased mortality due to comorbidities such as heart disease, stroke, depression and diabetes.

While the indications facing the ankle joint are varied, numerous, and prevalent, there is a lack of personalized solutions. For example, in the event of ankle fracture or osteoarthritis, a common solution is ankle arthrodesis (ankle fusion). In this invasive procedure, the bones of the joint are fused into one piece. The median cost of the procedure is over $40,000. While the procedure may reduce pain within the joint in the short term by eliminating the articulation of arthritic surfaces, the procedure presents lasting challenges including lack of mobility of the ankle, reduced stability, and reduced function. Additionally, the changes to the individual's gait due to reduced joint flexibility lead to adverse biomechanical forces in other joints of the lower body including the knee, hip, and back. As a result, the individual's overall mobility health and long-term quality of life declines.

While fusion surgery is used in extreme cases, ankle braces present an alternate solution to treating ankle instability and osteoarthritis. Many existing ankle braces focus on immobilizing the joint completely. While this avoids the cost associated with fusion surgery, these braces are less effective, yield mixed opinions between prescribers as to whether they are effective or not, present the same problems in limiting mobility in all axes of the joint, and do not present a personalized solution to the unique needs of the individual.

Ankle braces are designed for a multitude of functions and indications in daily life. They may prevent foot drop, assist plantarflexion, or stabilize the joint. It is typical for an ankle brace to prevent exaggerated motion in a direction of the ankle joint, such as medial/lateral rotation or plantar/dorsiflexion, in order to prevent injury during use of the brace or help the user recover from an injury. While limiting range of motion in certain aspects, the ankle brace should minimally interfere with the user's daily activity. Although current braces may be able to address specific indications and limit movement to prevent further injury and/or support recovery while activity is maintained, they are often bulky, rigid, and not customized to address the user's specific deficiency or need. Additionally, they are often static devices that are not adjustable by the user or clinician to best address the user's need, desired activity or state of movement. There exists a major market need for a dynamically adjustable ankle brace that can address a series of indications in a low-profile design, which does not interfere with other daily functions of the user. According to the current invention, the directionality and magnitude of corrective forces to support, augment, and limit joint movement can be tailored to optimally address the user's need and desired function.

In regards to specific currently available ankle braces, Ultra Ankle® currently sells three models of their ankle brace, two models for moderate support and one model for maximum support. These braces vary from being form-fitting to more rigid, and are recommended to users based on how many prior ankle injuries they have had. While these braces do have an adjustable strap, they do not offer a method for adjusting tension to control rotation around the ankle. Furthermore, this brace only allows movement along one axis allowing plantar- and dorsiflexion. The maximum support version of this brace offers a removable cuff for extra support during rehabilitation from an ankle injury, that may be removed when more mobility is desired.

DonJoy® performance offers a variety of ankle braces, comprising a variety of materials ranging from rigid cuffs to slip-on materials. While DonJoy sells ankle braces for a variety of needs, it is important to notice that most of their adjustable braces comprise a strapping or lacing system for tightening the orthosis on the joint, which is unlike the current invention using a tensioning apparatus that can quickly be adjusted via an adjustment mechanism across one or a multiple of axes, allowing for precise control of the force direction and magnitude by the user.

U.S. Pat. No. 9,707,118 describes a boot-like AFO designed for children with a tension element that has limited adjustability. Unlike the multi-axis rotation control brace disclosed herein, the device described in U.S. Pat. No. 9,707,118 provides a constant low force along one axis of rotation to pull the foot into a dorsiflex position while at rest for the purpose of improving range of motion and preventing heel cord shortening. In addition, the elastic band of U.S. Pat. No. 9,707,118 is not meant as a dynamic energy storage element to provide control of the ankle joint's rotation, but to provide a constant force to stretch the foot into a predetermined position when at rest.

Other currently available products in the field serve to protect or rehabilitate the ankle through a variety of methods. More specifically, some braces have introduced components under tension around the ankle joint. One on market technology, the Sutti Bounders by Fabtech Systems, incorporate an elastic band at the heel of the device. This device is used only for the pediatric market for strengthening, as the device is not designed to address conditions such as foot drop, ankle osteoarthritis, ankle instability or other common indications. The device lacks a dynamically adjustable tensioning apparatus, as is described in the current invention. The direction of force cannot by changed, and rotation can only be controlled around the ML axis statically in one direction. Additionally, the design is limited to a low-power elastic band, which is insufficient to support the range forces required to address a range of indications and patient populations beyond pediatric strengthening. The embodiments of the multi-axis rotation control brace described herein are designed to support high forces significant enough to treat these broader patient populations while providing for dynamic adjustability by the user.

US20180333285A1 describes an apparatus for a human orthosis for control of foot drop. The application teaches that by rotating a dial, "the upper retention structure is configured to tighten around an anatomy of the user when the sock moves into a plantar flexed position", so the resistance of the strap tightening circumscribing the calf is used to limit plantar flexion. This is different than the device disclosed herein, where, in aspects, the tensioning system applies a force directly to the distal portion, or to an elastomeric portion attached to the distal portion, and the direction of that force is modifiable by placement of anchor points, enabling control on multiple axes. Unlike the multi-axis rotation control brace described herein, this application does not demonstrate adjustability of the direction of force, or application of the mechanism for conditions beyond foot drop. In other words, the device cannot be tailored by a clinician or the user based on the specific direction and magnitude of force required for the user. Additionally, the multi-axis rotation control brace described herein incorporates tensioning and compression systems, which contain energy storage elements, e.g. an elastomer or a spring. Such elements provide more natural control of the ankle joint's rotation, having similar properties to those of tendons, ligaments and muscles.

The same limitations apply to an on-market technology, the SaeboStep® brace. The device is further limited, as it is not custom (off-the-shelf or one size fits all) and is not personalized to the user's need, as described in the multi-axis rotation control brace described herein. The SaeboStep has no distal portion, as described herein.

SUMMARY OF THE INVENTION

The device described herein is a multi-axis rotation control ankle orthosis that can control forces around the ankle joint, as well as be customized to the user's needs in various aspects. It can be adjusted by the user, manufacturer or clinician through multiple features including: 1) a tensioning or compression apparatus where the user can adjust the magnitude and direction of corrective force based their activity or indication, 2) optionally, a mechanism for changing the direction/orientation of corrective force or forces through a series of anchors, anchor points, channels, slots, or other positioning or connecting elements, and 3) optionally, a method to custom-fabricate the shape or form the device to the user's anatomy to optimize the comfort and efficacy.

In some embodiments, the ankle orthosis is designed to limit motion in a specific direction, for example to prevent over rotation and counter rotation of the ankle joint; this is accomplished by applying different amounts of tension or compression around different regions of the ankle, and between some part of the foot or footwear and a part of the ankle, the proximal part of the ankle, or a part of the leg situated above the ankle. Tension is applied to manipulate the position of the foot relative to the tibia and fibula. The applied tension can be fixed, adjustable, or dynamically adjustable in that tension increases with increasing motion between the ankle-foot-leg system. In other embodiments, the same directional forces may be applied to augment motion of the foot-ankle complex in a desired direction. Through this mechanism, the brace allows mobility within certain axes while limiting it in others to maximize the freedom of the joint while providing only the necessary directional stability.

Some embodiments comprise a proximal portion and a distal portion, where the proximal portion is affixed above the ankle joint and houses the adjustment mechanism, in aspects. The proximal portion is connected to the distal portion by tensioning or compressive elements, through which forces optionally can be controlled by the user via the adjustment mechanism. In other embodiments, the device is comprised of one continuous mesh, sock or sleeve through which tension can be controlled by the user. In other embodiments, tension is generated between the proximal and distal portions of the brace or sock without a tension-adjusting mechanism. The amount of tension may be tailored to an individual's needs. The tensioning or compressive elements may be external, or partially- or fully-integrated within the brace or sock.

The device applies a tension that can hold the ankle and foot in a position that prevents or reduces the likelihood of injury, such as an ankle roll, or can prevent or reduce the likelihood of overuse injuries such as repeated over-supination or over-pronation. The device can also address conditions like foot drop by applying a significant force in the appropriate direction to counteract the front of the foot from dropping down. The foot drop device, for example, may generate a force across more than one axis for users who have a combination of foot drop and eversion. The same mechanism, applied differently may also augment activity in those with muscle or neurological deficiency, e.g. augmenting plantarflexion or dorsiflexion.

The described device may be customized to optimally address the user's needs. This includes features such custom fabrication from a 3D-scan or measurements, custom fit through modification by a certified professional (e.g. thermoforming), adjusting the amount of force applied in a given direction using an adjustment mechanism connected to a tensioning element (e.g. containing elastic bands) or compression element (e.g. containing springs), or changing of the direction in which force is applied, including the axis about which a moment is generated. Tensioning or compression elements may be in the form of bands, sheets or lines and integrated within or external to the brace or sock. The size and geometry of these elements may be tailored to yield specific mechanical properties. Inelastic and elastic components may be combined in patterns or arrangements to control tension in areas where it desired.

Mechanism for Adjusting the Magnitude of Force

The tensioning apparatus on the device allows for multiple aspects of customization for adjustment by the user, manufacturer or a certified professional (e.g. a doctor or physical therapist) for desired function, whether limitation of movement, augmentation of movement for rehabilitation, or performance enhancement. Among others, a novel aspect of the device relates to the ability to dynamically adjust the amount of tension in one or more directions around the joint, described herein as a multi-axis rotation control device. The term multi-axis means that tension can be generated across at least one axis. The amount of force generated in a given direction may be controlled dynamically or statically via energy storage elements in compression or tension. Energy storage elements are described as any element or component that stores mechanical energy including, for example, elastomeric bands, webs or other geometries, springs, pneumatic elements, electromagnetic elements, pneumatics, or any component that may act as a mechanical energy storage element that may be adjusted to hold variable forces. In aspects, the force within the element will be set by the user at a certain position, and will change throughout a range of motion.

For example, a series of bands on the lateral side of the ankle may be placed under tension to prevent inversion of the ankle to address issues of chronic ankle instability. In the same way, a compressive element (e.g. a spring) placed on the medial side of the ankle may also limit or prevent inversion of the ankle to address the same indication. By adjusting the magnitude of force within the energy storage element, the user can compensate for ligament, tendon, muscular or neurological deficiencies, for example.

The user can adjust the magnitude of force within the tensioning or compression element via a dial, lever, ratchet and pawl system, pulley, electric motor, etc. to dial in the amount of force supplied. The amount of force may be recommended by a prescriber or other professional and indicated on the device. The range of forces able to be applied by the mechanism may be prescribed by a professional, e.g. forces of 5-10 pounds may be achieved in the element through a construction or inclusion of certain components by the manufacturer or professional to support a rehabilitation regiment in line with the individual's need. Other patients may benefit from less than 5 pounds or more than 10 pounds of tension. In other words, the device may incorporate tensioning elements of varying storage modulus, size, cross section, material or mechanical properties in general. By example, a tensioning element that may be adjusted with forces between 0-1 pound. to assist in dorsiflexion may be used for weeks one and two of a rehabilitation regiment. The element may be replaced as rehabilitation progresses with bands of higher storage modulus, e.g. one that can hold up to 5 pounds of tensile force to aid in muscle strengthening.

In aspects, the user may be able to rapidly and conveniently adjust the device during activity. For example, the user may engage tension in the device while walking, increase tension further while walking uphill, and disengage tension while seated within a span of seconds. The tensioning apparatus may also have preset values or ranges. The tensioning apparatus may be adjusted manually or automatically via a system of at least one sensor and motor or actuator.

The adjustment mechanism may be used by the individual to optimize for a certain activity, to be used at a certain stage of rehabilitation, or based on the current medical condition (e.g. if the user has a greater degree of pain on that day, they may add more tension to the element to further unload the joint). The degree of force generated or stored within the tensioning or compressive element may be modified based on a user-controlled dial. This allows the user to change the force from zero to maximum based on activity. The degree of unloading may be modified by interchangeable elements, e.g. springs or bands of different spring constants. In addition to being able to adjust tensile force from zero to maximum continuously to achieve any force within the range, the device may allow for tensioning to specific discrete forces (e.g. in 0.1 lb., 0.2 lb., 0.3 lb., 0.4 lb., 0.5 lb., 0.6 lb., 0.7 lb., 0.8 lb., 0.9 lb., 1.0 lb., 1.1 lb. increments), or may simply toggle between on and off (e.g. minimum and maximum force). The force may be adjusted in any number of increments including on or off, stepwise between a minimum and maximum force, or continuously on a gradient.

The tensioning elements may be constructed of different materials to provide different properties based on the user need. For example, a tensioning element consisting of an elastomeric element of certain viscoelastic properties may better mimic the feel of natural muscle, tendon, and ligament complexes, while a more rigid or fully rigid tensioning element may completely lock the foot in one or more directions or prevent movement beyond a specific range of motion.

Mechanism for Adjusting the Direction of Force

The direction of force may be modified statically or dynamically by the user, manufacturer, or a certified individual to address a specific need. In one aspect, a tensioning element may be oriented on the lateral side of the ankle or foot to address chronic ankle instability, unload the medial part of the ankle, or prevent inversion. See FIG. 1 for labelling conventions of the 3 axes of the ankle joint. In this embodiment, a torque applied about the AP axis would support a weak ankle (e.g., weak ligaments within the ankle, inferior muscle strength, and/or bone or cartilage damage). The anchor may be connected at anchor points between the two elements: one at the proximal cuff and one or more at the distal portion, which yield a net force generated around the AP axis to prevent inversion. Multiple anchor points may be distributed along the proximal or distal cuff to provide greater stability and force distribution. This distribution may be created as a function of the geometry of the tensioning or compression element, which yields a net force vector controlled through one or more adjustment mechanism that optimally reduces inversion or eversion. For example, the shape and position of an elastomeric band, sheet or web between the proximal and distal portions will determine the force magnitude, direction, and overall distribution depending on the path it generates between the proximal portion and distal portion. The cables or tensioning elements may be routed through rigid or flexible material, or along the side or surface of the brace or sock to generate the desired force profile across the proximal and distal portions of the device. For example, the device meant to prevent foot drop will have cables and/or tensioning elements routed near the front of the foot above the ankle that have anchor points in the distal portion of the device, in a position that is forward from the position where the cables or tensioning elements connect in the proximal portion of the device.

In other aspects, the device may support dorsiflexion, for example to address foot drop, by being anchored to the front part of the foot or footwear and generate an adjustable torque along the ML axis. The user can increase tension to provide additional support for dorsiflexion and offset the muscle deficiencies that cause foot drop to restore a normal gait.

The tensioning or compression element may be anchored between the proximal and distal portions to limit or support abduction or adduction. For example, if an individual had insufficient adduction, the element may be placed on the medial side of the foot, aligned with the tibialis anterior muscle, to supplement this movement.

As a multi-axis, rotation control device, the tensioning or compression elements may be anchored in a way that supports multiple directions of movement in the face of multi-directional deficiency. For example, it is common that individuals with foot drop also experience difficulty in adduction. In this instance, a tensioning element may be anchored on the lateral side of the proximal portion and the medial side of the distal portion. By generating force across this element through tensioning, the individual's joint position at rest will be restored to the normal position. The anchor point in either direction can be modified depending on the severity of muscle deficiency or need for correction in either direction. FIG. 3A shows one embodiment of a multi-axis rotation control orthosis to achieve this function. In this case, the device supplements movement around all three axes (the vertical, ML and AP axes), which is often the case in individuals with ankle conditions, due to the natural orientation of muscles around the joint. In this case, the device augments the tibialis anterior, which is often weakened in individuals with foot drop. However, there are multiple other muscles, ligaments, and tendons with different orientations and anchoring along the foot-ankle complex that may need to be augmented. A dynamically adjustable device allows each user's specific need to be addressed optimally in a single device.

In the proximal cuff, the tensioning elements may all be anchored at one point directly or indirectly to the adjustment mechanism. However, the direction of force and relative tension in each of the one or more tensioning elements may be modified by channels, grooves, guides or other structures on the proximal cuff, herein described generally as channels (see, e.g., FIG. 3A and FIG. 3B).

The anchor points may be determined to optimize function through algorithms, artificial intelligence, machine learning, and general software-automated design of the fabricated device.

The anchor points or connection of the tensioning element may be modified and placed at any point or angle of the proximal or distal portion of the device. There may be unlimited orientations and positions across the surface of the device. Alternatively, the anchor points may be pre-set to limit options for force direction. For example, the tensioning element may be anchored to position A to prevent inversion, or it may be placed at position B to do all of the following: limit inversion, support abduction and support dorsiflexion (see FIG. 3A and FIG. 3B for example).

Adjustment Mechanism

In order to control forces and rotation around one or more axes, the device may contain multiple tensioning or compression elements to address the user's need. In aspects, one or more tensioning or compression elements may be controlled by a single adjustment mechanism. The tensioning elements can be modular and added as needed based on the user's condition. Additionally, the device can contain one or more adjustment mechanisms of the same or varying design (e.g. rotary dials, levers, ratchet and pawl mechanisms, or motors) that change the magnitude of force within the tensioning or compression element(s) around one or more axes. The adjustment mechanisms may also change the direction of force by moving anchor points, changing tensioning or compression element(s) geometry, or changing orientation of the tensioning or compression element(s).

The user may be able to remove the adjustment mechanism, or may be able to move the adjustment mechanism from one point on the device to another. Multiple adjustment mechanisms may be incorporated on the device to modify force in multiple directions. The adjustment mechanism may be in the form of a slot with a corresponding external component, e.g. a key that can be inserted at multiple locations of the device to adjust forces in different orientations, engage or disengage different tensioning or compression elements, or change the direction of force.

Custom Fit

The device may be further customized through a user-specific fit. The shape of any of the proximal portion, distal portion, sock, or tensioning or compression element may conform to the user's body. A 3D scan may be used to manually, automatically, or semi-automatically fabricate a custom device, for example through 3D printing, or additive manufacturing, or subtractive manufacturing. In aspects, the device may consist of both custom and non-custom elements. For example, a custom foot orthotic may be coupled with an off-the shelf cuff, as well as other variations. The custom fit will ensure user comfort and maximize effectiveness by controlling contact area and resulting force distribution where the device is affixed to the user. For example, the proximal cuff may be designed to be affixed to less sensitive parts of the user's ankle, to avoid scarring or injury, or it may be designed to distribute forces optimally around the ankle while tension is applied on one side to prevent adverse rotation and discomfort. Similarly, the distal portion may be custom-fit based on the intended geometry or support needs of the user under load, as prescribed by a doctor or determined through analysis of user data. For example, a custom foot orthotic may be included with the ankle orthosis based on a scan of the user's foot to improve gait or unload or improve biomechanics of the joint in combination or individually from functional ankle orthosis. Custom design and fabrication may not just determine personalized fit, but also the direction of force across or between the joint. For example, anchor points or channels in the device to guide the tensioning element may be automatically or semi-automatically positioned in the device based on user need, prescription, gait analysis or other data. The overall shape of the device, for example the proximal cuff, may be automatically designed based on scan data, user morphology, radiographic data, prescription data, or user-provided data (e.g. pain within a region of the joint) to automatically adjust forces around and within the joint. Additionally, the adjustment mechanism may be placed optimally using similar data and automated design processes.

The device may be prefabricated and can be further modified by the user or a professional to provide the desired function. Modification may include molding or thermoforming of the rigid components of the device to improve fit, comfort and function. Modifications may further include adjustment of anchor points to create the intended correction or unloading in the individual. The device's modular design can allow a certified fitter or doctor to modify the device's performance based on the specific user need.

The device may be connected to or used in conjunction with additional orthopedic or prosthetic devices using universal or custom connectors. The device may be modular for compatibility with different devices based on the connection required. Other devices which may be connected to the device include a knee orthosis to yield a knee ankle foot orthosis (KAFO), a knee hip orthosis to yield a hip knee ankle foot orthosis, or may connect to prosthetic devices, e.g., prosthetic feet. The device may also be continuously fabricated with such other devices. Any one of these orthoses may contain a similar adjustable tensioning mechanism, which can be used individually or adjust with a single connected adjustment mechanism.

Motors and Sensors

The tensioning or compressive elements may increase or decrease force across, between, or within the proximal and distal portions through adjustment by a motor. The motor may be controlled by an electronic interface connected directly or indirectly to the device. The interface may be an app or software on the user's mobile device, smart watch, or other computer/smart device. In aspects, the device may comprise one or more processors, one or more motors, one or more controllers, one or more sensors, one or more antennas, as well as software to control, instruct, process, command, implement adjustment of the tensioning element (s) of the device.

The motor or elements may control or change force within the tensioning or compression element(s) automatically based on input from sensors located on the device or elsewhere on the user. For example, EMG sensors and/or accelerometers may detect stages of gait to optimize positioning of the foot and resulting gait throughout a range of motion. In another example, sensors may trigger the energy storage units to engage while stepping to support plantarflexion at one stage of gait and support dorsiflexion at another. In other aspects, the tensioning element can be manually adjusted using, for example, a smartphone, smart wearable technology, computer, external processor, or an electronic control mechanism on or attached to the device. These adjustments can be made in real-time or substantially real-time as understood by one of skill in the art; they can be made by the user or a treating practitioner; and/or they can be made while the user is wearing the device. A combination of both automatic and manual adjustment is also contemplated.

Method of Making

The various embodiments of the present disclosure may use traditional manufacturing processes for ankle braces and/or 3D printing/additive manufacturing to produce the components and/or the overall device. These techniques may also be used to fabricate positives through which negative molds are constructed for injection molding.

The fabrication technique allows low-cost, custom devices. It also enables manufacturing of intricate parts containing internal channels and features that could not be feasibly or affordably produced with injection molding, machining, or other traditional methods of manufacturing orthotic devices. 3D printing enables efficient production of lightweight, yet durable materials such as thermoplastics. The result is a highly effective, lightweight, customized, and cost-effective device that can be manufactured at scale.

BRIEF DESCRIPTION OF THE DRAWINGS

The above and other features, aspects, and advantages of the present invention will be further clarified through the following drawings, detailed description, and claims. The accompanying drawings illustrate certain aspects of some of the embodiments of the present invention and should not be used to limit or define the invention. Together with the written description the drawings serve to explain certain principles of the invention.

FIG. 3A displays application of the embodiment to prevent inversion while FIG. 3B displays application of the embodiment to limit plantarflexion.

FIG. 4B further displays one potential mechanism for adjustable connection of the channel guide to the sock, with a movable hook or loop surface of the cable guide as described in embodiment 3. FIG. 4C displays an application of the embodiment for foot drop or controlling rotation around the ML axis.

FIG. 5A is an application for controlling foot drop, inversion, and or eversion while FIG. 5B is an application for controlling inversion.

DETAILED DESCRIPTION OF VARIOUS EMBODIMENTS

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Embodiments comprising various features may also consist of or consist essentially of those various features. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention.

All references cited in this specification are hereby incorporated by reference in their entireties.

As used herein, the term "proximal" is synonymous with top or upper, as in above the ankle. The term "distal" is synonymous with bottom or lower, as in below the ankle. As used herein, the term "anterior" refers the front of the foot, ankle, or device while "posterior" refers to the back.

Throughout the following detailed description, it should be understood that elements in tension are by example and that the same rotational force may be generated by a compression element on the opposing side of the ankle.

It should also be understood that the adjustable tensioning and compression apparatuses herein are described in ankle orthoses by example only. One skilled in the art would recognize that similar adjustable tensioning and compression apparatuses could be applied to control rotation and forces around other joints including the wrist, shoulder, back, neck, knee, hip, and elbow. For example, the adjustable tensioning apparatus described herein could be used in an assistive knee orthosis.

Throughout the following detailed description, the same reference numbers refer to the same elements in all of the figures.

EXAMPLES

Figure 1:
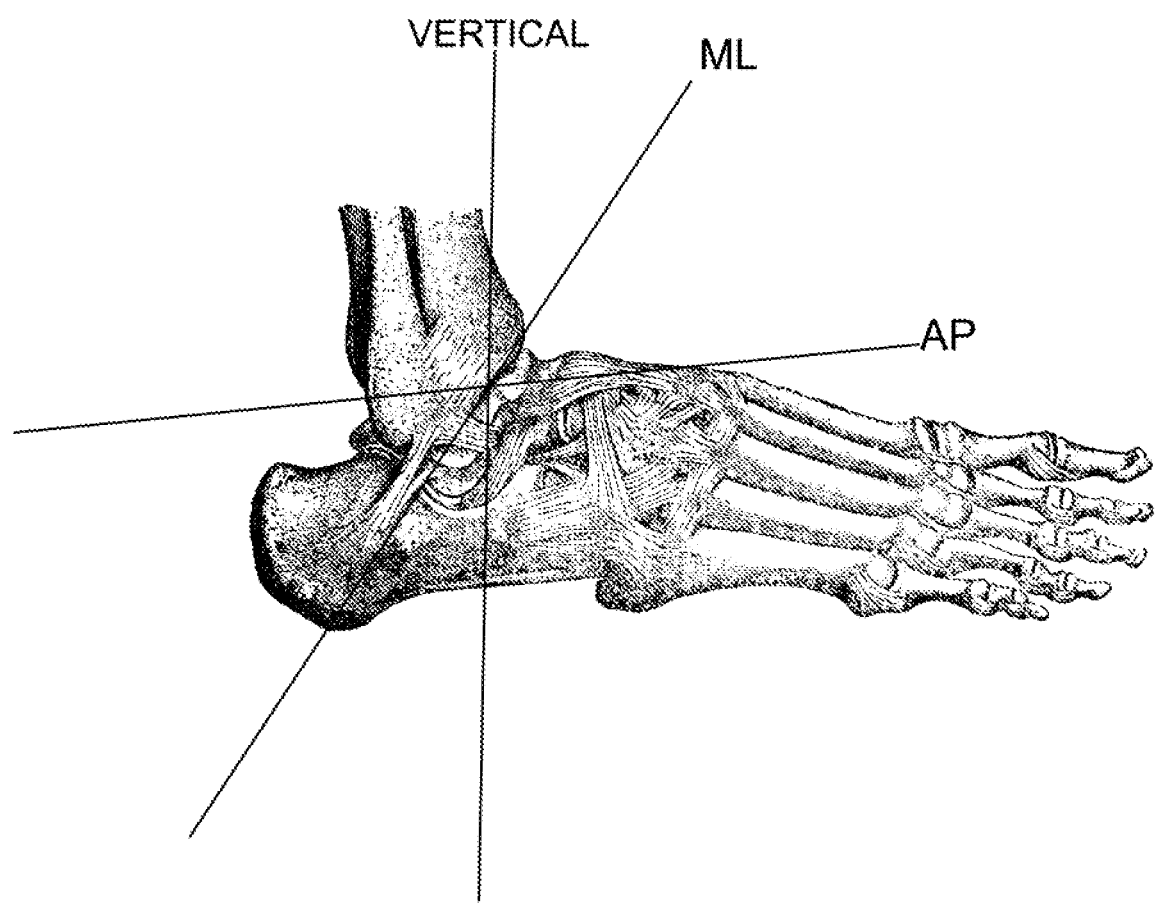
FIG. 1 illustrates an anatomy of an ankle joint according to embodiments described herein and designates three axes of rotation: the coronal (ML) axis, the sagittal (AP) axis, and the vertical axis.
Figure 2:
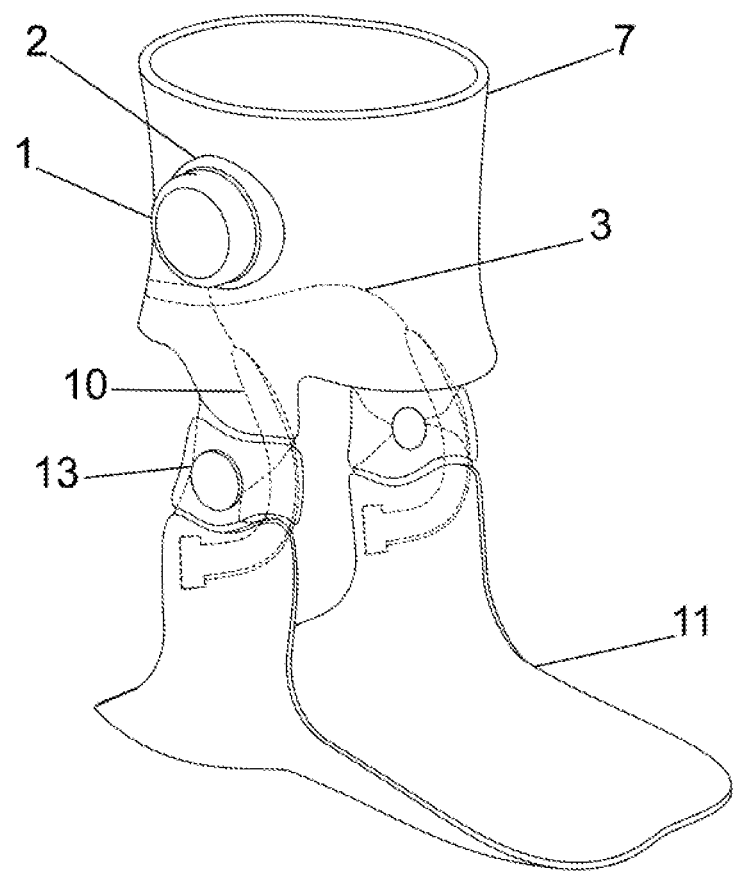
FIG. 2 illustrates a lateral view of a rotation control orthosis comprised of a proximal cuff and a distal portion, connected by an adjustable tensioning apparatus. The tensioning apparatus is comprised of a rotary adjustment mechanism, and cables attached to a tensioning element, which is anchored in the distal portion.

Preferred Embodiment One: Multi-Axis Rotation Control Ankle Brace with Proximal and Distal Portions and Hinge Preferred embodiment one (FIG. 2) is comprised of a proximal cuff (7) and distal portion (11) connected by a hinge (13). The device contains an adjustable tensioning apparatus (3,9,10) that runs across the one or more hinge that is positioned medial and/or lateral to the ankle joint. The tensioning element in this case represents one type of energy storage element, in this case under tension. The tensioning element in this example further comprises a tensioning element (10), a rigid cable (3) and an adjustment mechanism (1). The adjustment mechanism (1), in this case a rotary dial, is embedded in an adjustable mechanism insert (2) within the proximal cuff (7). It may be held in place by the form of a locking mechanism, where the dial's male end is complementary with the female insert in the proximal cuff (7). It may be sewn or glued or otherwise bonded into the proximal cuff. Regardless of the method, the adjustable mechanism insert (2) ensures that the adjustment mechanism (1) is securely in place when subjected to any force subjected by the user intentionally or inadvertently by the user, including but not limited to rotation in either direction, or pulling out. The adjustment mechanism (1) is further connected to the cable (3), for example by a knot. The term cable herein generally refers to any type of cable, wire, braid, string, chain, lace, rope, or article that is substantially flexible yet not extensible and is able to be wound up and transmit tensile forces.

The cable or cables are attached to the one or more tensioning element, which is inserted into the distal portion, and may be anchored in a slot within the distal portion. When tension is applied to the tensioning element, a counter-clockwise torque is generated around the hinge. This torque would generate rotation around the ML axis to support dorsiflexion and resist plantarflexion. One skilled in the art would understand that anchoring the tensioning elements in the opposite orientation around the hinge and generating a clockwise force would have the opposite effect: generating rotations around the ML axis to support plantarflexion and resist dorsiflexion.

The adjustment mechanism (1) allows the user to change the magnitude of force within the tensioning element, and therefore the force around the joint based on their need. In some embodiments, the adjustment mechanism allows tension to be increased in one direction, e.g., by clockwise rotation of a dial. The tension may be released rapidly by disengaging the dial, e.g., by pulling it out, pushing it in, or pressing a button. In other embodiments, the adjustment mechanism may allow gradual increase or decrease of tension. For example, clockwise rotation of a rotary dial would increase tension, while counterclockwise rotation of the dial would reduce tension. The adjustment mechanism may be a rotary dial, a lever, a switch, a ratchet and pawl mechanism, a pulley, or an electronic adjustment mechanism operated by a motor. The adjustment mechanism may be placed in an optimal position for use that is non-obstructive during activity, but accessible, for example at the rear of the proximal cuff.

Preferred Embodiment Two: Multi-Axis Rotation Control Ankle Brace with Proximal and Distal Portions Preferred embodiment two (FIG. 3A) is comprised of a proximal cuff (7) and distal portion (11) connected by a tensioning element (3,9,10) that runs across or near the ankle. Unlike embodiment 1, (FIG. 2), the proximal cuff and distal portion are connected by the tensioning element rather than a hinge. However, the embodiment contains functionally equivalent descriptions of the components of the adjustable tensioning apparatus including the adjustment mechanism (1), the adjustable mechanism insert (2), one or more cable (3), and a tensioning element. The tensioning element in this case represents one type of energy storage element, in this case under tension.

The way the cable or cables are connected to the adjustment mechanism may change how forces are applied on one or more cables, e.g., adding tension to one while decreasing tension on another, or providing equivalent tension to both cables. In the same way, tension may be increased on one side of the cable and decreased on the other side of the cable.

The cables may be connected directly to the distal portion, therefore directly connecting the adjustment mechanism and the distal portion. The cables may also be indirectly attached to either the adjustment mechanism and/or the distal portion. Indirectly attached is herein defined as being connected to described components, e.g. a cable may be indirectly attached to the distal portion by attaching to a tensioning element, wherein the tensioning element is directly attached to the distal portion. In aspects, these may be connected in line with one another. Such an example is shown in this embodiment (FIG. 3A), where the cable is indirectly connected from the adjustment mechanism (1) to the distal portion (11) by a tensioning element (10) and anchors (9).

The anchors, as described herein, generally refer to any type of anchor, hook, hook and loop materials, button, screw, knot, fastener, insert or connecting mechanism that exist between components of the tensioning apparatus, proximal portion, and/or distal portion. The location of the anchors (9) on the tensioning element (10), proximal cuff (7) or distal portion (11) may be changed to control the direction of force around the joint. They may be set during fabrication or may be moved by the user or professional as necessary to change the direction of force.

The tensioning element (10) is connected to distal portion (11). As such, the proximal cuff is connected to the distal portion by the tensioning element, which runs across or near the ankle joint. By example, the tensioning element may be connected to the distal portion with hooks, hook and loop materials, screws, knots, fasteners, inserts or anchors or simply a melding of material with the tensioning element. The tensioning element and the distal unit may also be manufactured as one continuous piece, for example as a 3D printed or molded thermoplastic material.

The adjustment mechanism (1) allows the user to change the magnitude of force within the tensioning element, and therefore the force around the joint based on their need. In some embodiments, the adjustment mechanism allows tension to be increased in one direction, e.g., by clockwise rotation of a dial. The tension may be released rapidly by disengaging the dial, e.g., by pulling it out, pushing it in, or pressing a button. In other embodiments, the adjustment mechanism may allow gradual increase or decrease of tension. For example, clockwise rotation of a rotary dial would increase tension, while counterclockwise rotation of the dial would reduce tension. The adjustment mechanism may be a rotary dial, a lever, a switch, a ratchet and pawl mechanism, a pulley, or an electronic adjustment mechanism operated by a motor. The adjustment mechanism may be placed in an optimal position for use that is non-obstructive during activity, but accessible, for example at the rear of the proximal cuff.

One or more channel (4) in the proximal cuff guides the positioning and orientation of the cables, therefore controlling the direction of force. The channel may be unique to the specific model of brace, or it may be custom to the individual based on the precise direction of support that they require.

Figure 3A:
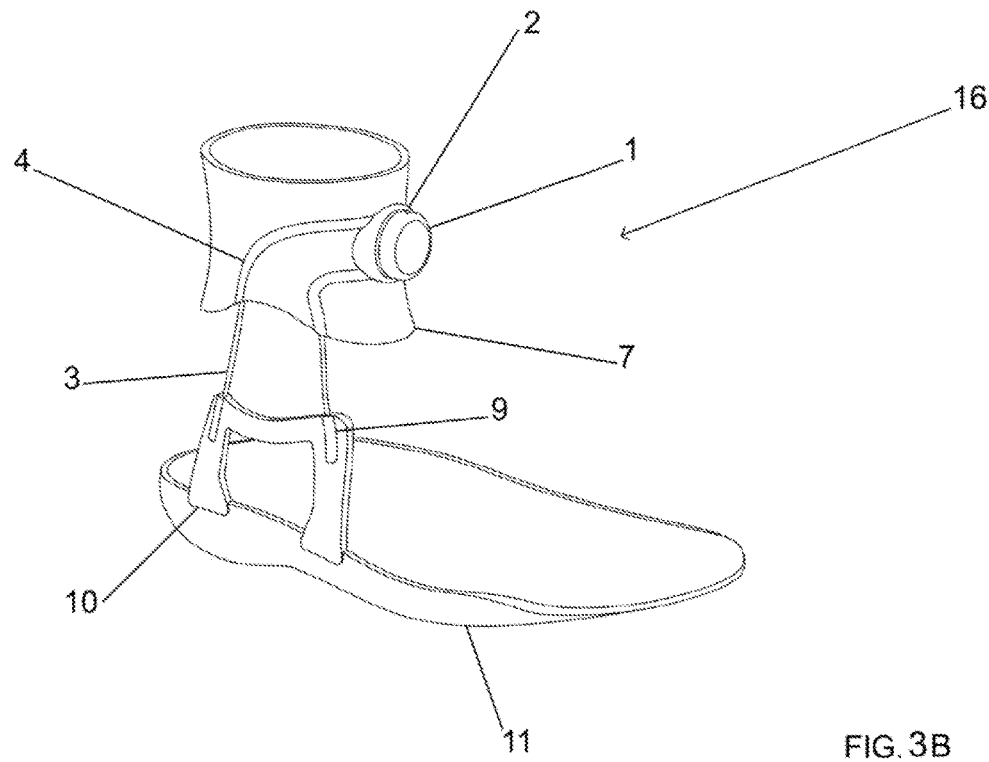
FIGS. 3A and 3B display a lateral view of two variants of a multi-axis rotation control ankle orthosis comprised of a proximal cuff and a distal portion, connected by an adjustable tensioning apparatus. The tensioning apparatus is comprised of an adjustment mechanism, a cable, a tensioning element, and anchors to connect the components.

By way of example, a proximal fabric (semi-rigid) cuff (7) may anchor the device to the ankle (as shown in FIG. 3A). The proximal cuff may also be connected to the calf or at another position above the ankle joint. The proximal cuff may be rigid or semi rigid to fit optimally to the user's ankle, calf, or any part of the leg. The distal portion (11) will attach or conform to the user's foot or provide additional support and to maximize comfort. By example, the distal portion may comprise a foot orthotic. The distal portion may be comprised of a rigid or semi-rigid custom or off the shelf orthosis, insert, sole, fabric, or shoe. The distal portion may work synergistically with the adjustable tensioning mechanism in order to optimize the joint geometry, modify forces within other lower limb joints such as the knee and hip, and modify gait overall.

Figure 3B:
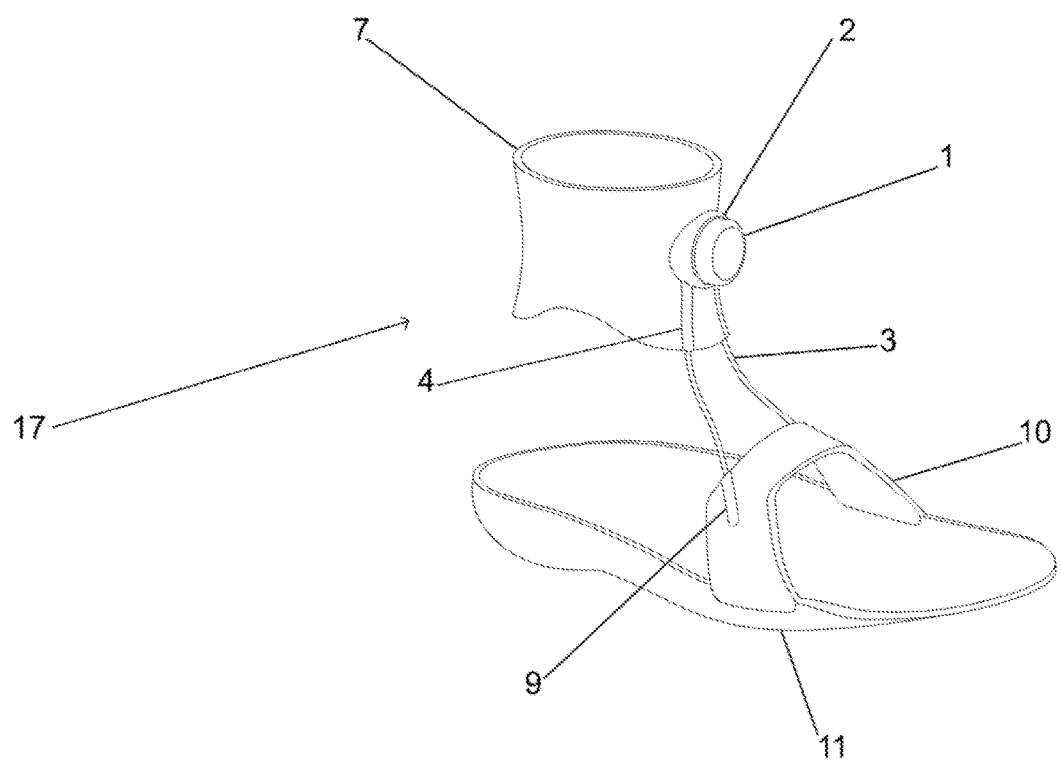

The energy storage element, in this example a tensioning element (10) may comprise rigid, semi rigid, elastic or spring elements individually or in combination. Force may be stored within the energy storage element to generate a torque or force around the desired axis or combination of axes of the joint. The modularity of the device enables this axis of rotation to be changed, either in manufacturing, by the clinician or by the user. For example, by positioning the tensioning element on the lateral side of the foot, inversion can be limited or prevented (FIG. 3A). Alternatively, the tensioning element placed anterior to the ankle may prevent foot drop (FIG. 3B). The direction of the net force vector and positioning of forces around the joint to control range of motion may be modified by positioning of the channels or guides within the proximal portion through which the cable or cables run. Additionally, direction of the net force vector and positioning of forces around the joint to control range of motion may be modified by the shape of the tensioning element (10), for example an elastomeric band with one point of connection between the proximal and distal portions vs. an elastomeric web with two points of connection to the distal portion (as shown in, e.g., FIG. 3A) vs. an elastomeric sheet continuously connected along the distal portion would change the distribution and direction of the net force vector.

Overall, the embodiment allows for customization to fit the user's specific need in many aspects. The magnitude of force can be modified by the adjustment mechanism (1) and also by the material properties and geometry of the tensioning element (10). The direction of force and axis of rotation can be modified by the adjustment mechanism, the channel (4) location on the proximal cuff (7), the location and number of anchor points (9) between the cable (3) and the tensioning element (10), the geometry of the tensioning element (10), and/or the location of the connection between the tensioning element (10) and the distal portion (11). Through these mechanisms, rotation can be limited or controlled in one or more of the ML, AP and vertical axes to stabilize, correct, or unload the ankle joint. The device can then therefore be engaged to restore proper foot and ankle orientation or joint geometry.

Figure 4A:
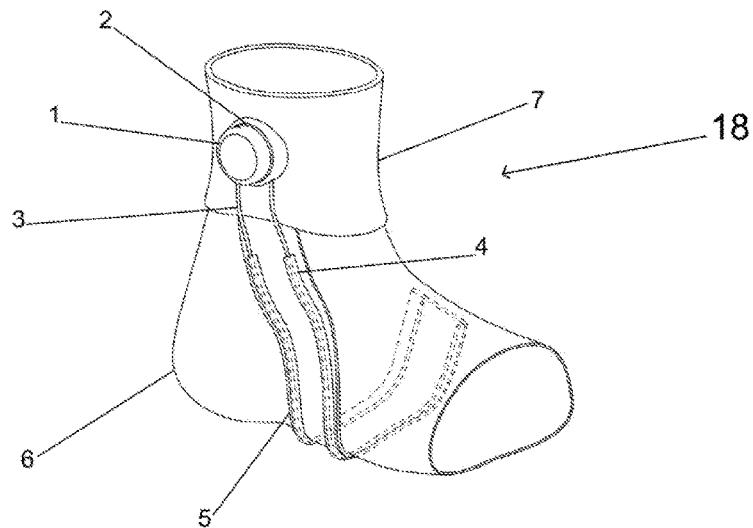
FIGS. 4A-4C illustrates a multi-axis rotation control ankle orthosis comprising a proximal cuff, a sock, and an adjustable tensioning apparatus. The tensioning apparatus is comprised of an adjustment mechanism, cable, and a cable guide, which connects to the sock.
Figure 4B:
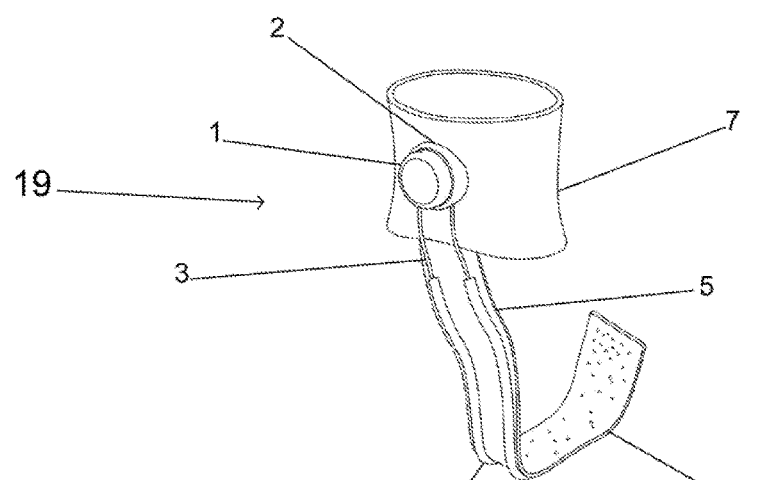

Preferred Embodiment Three: Multi-Axis Rotation Control Ankle Brace with Sock and Cable Guide Embodiment three is comprised of a proximal cuff (7) and a sock (6) that incorporates a tensioning element (1,3,4,5). (See, FIG. 4A) The proximal cuff may be connected to the sock e.g. by sewing, hook and loop, hooks, buttons, or other fasteners. The proximal cuff and connected sock may also be one continuously manufactured unit or material. In this embodiment, the tensioning apparatus is comprised of an adjustment mechanism (1), one or more cable (3), one or more channel or pathway, optionally a tensioning element such as an elastic band, and optionally one or more cable guide. The adjustment mechanism (1) and adjustment mechanism insert (2) are the same as described in embodiment 1 (See, FIG. 2). Similarly, the adjustment mechanism may be connected to one or more cables as described in embodiment 1. In the example shown in FIG. 4A, rather than connecting to a tensioning element as described in embodiment 1, the cables are connected to a cable guide (4). The rigid, semi-rigid, or mostly inelastic cable guide connects to the sock (6) in order to direct force around one or more axes. The cable guide may consist of an elastomer or fabric, containing a hook (8) on one side (as shown in FIG. 4B) to adhere to the sock containing loop on its surface, at any position.

Lace or wire may run through the channels (4) in the cable guide (5) and operatively connect to a rotary dial housed on the proximal portion, as described in embodiment one. In this way, the band can be tensioned to generate or limit rotation around the ankle depending on the path of the cable guide. In one embodiment, the band may be positioned on the lateral side of the foot and tensioned to limit or prevent inversion. If the band is positioned on the lateral side of the foot and in front of the center of the ankle joint (as shown in FIG. 4A), it can generate a torque around 3 axes to 1) limit or prevent inversion, 2) limit or prevent adduction, and/or 3) support dorsiflexion to limit or prevent foot drop; thus, a multi-axis rotation control device. This capability is valuable, as individuals with foot drop suffer to varying degrees with deficiency in dorsiflexion and abduction, not only dorsiflexion. The device, as shown in FIG. 3A would restore the foot of an individual with both of these deficiencies to its normal position and function. If positioned on the top of the foot, the device can prevent foot drop alone, focusing on dorsiflexion support and correcting rotation around the AP axis.

Figure 4C:
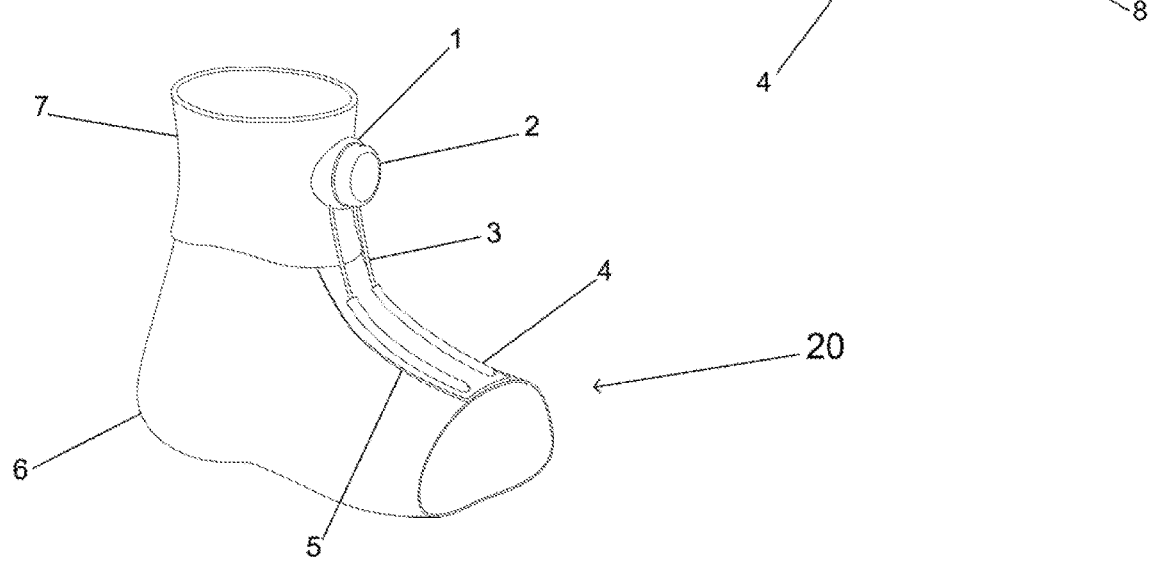
Figure 8:
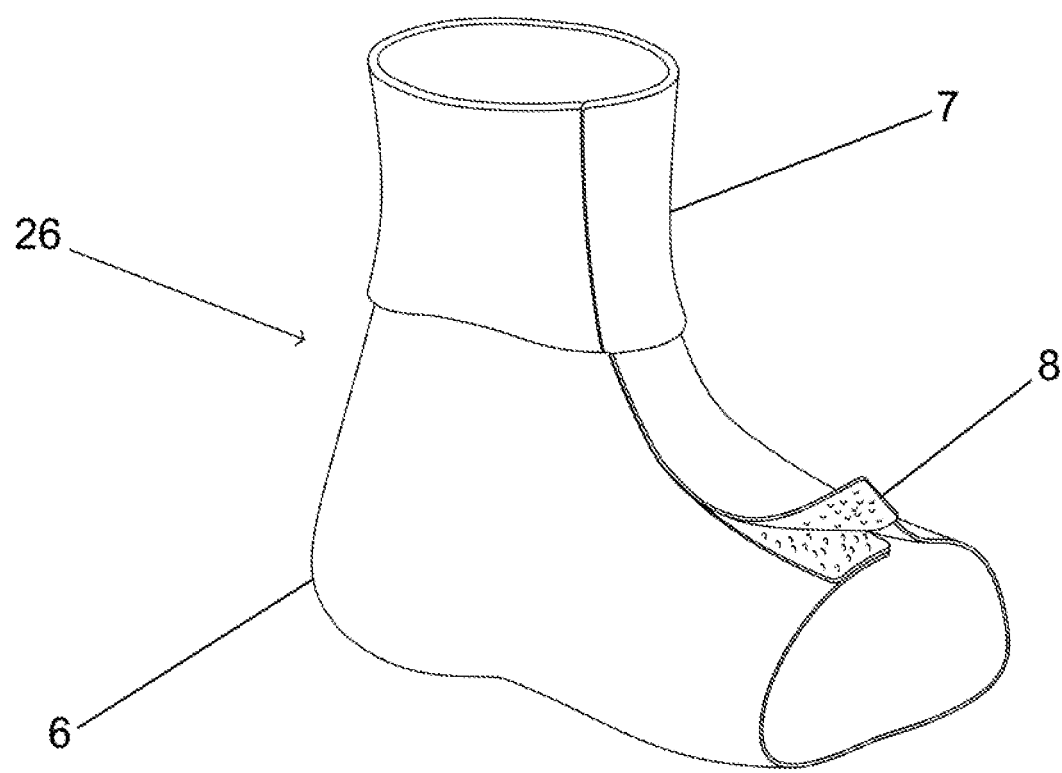
FIG. 8 displays a hook-and-loop opening for the user to easily don and doff the device.

The sock (6) may consist of rigid or semi-rigid materials. By example, it may be produced from a fabric. The fabric may be of universal size for all users and stretch to fit the size of the user's foot, or it may be produced in discrete sizes (e.g. from extra-small to extra-large). The sock may be comprised fully of a loop material, or may be coated with loop material, in order to connect to the hook material (8) on the cable guide (5). The sock may slide onto the joint as a mostly continuous member, or it may unfold and wrap around the joint, with one or more portions coming together to form a sort of sock or sleeve, which may be held together by hook and loop materials, for example as shown in FIG. 8. Other compatible materials may allow temporary or permanent connection between the sock (6) and cable guide (5). In some embodiments, the cable guide may connect at any point and orientation to the sock to precisely determine the direction of force around the 3 axes of the ankle joint. The cable guide may also generate pressure or compression in a target region of the joint based on its position in order to combat swelling, improve joint stability, or relieve pain. In other embodiments, the band can only attach to set positions on the sleeve with compatible material. Specific segments of the sock (6) may contain strips of compatible loop material to which the cable guide (5) can adhere. For example, position 1 may be located as shown in FIG. 4A to limit or prevent inversion for patient A, while position 2 may be located as in FIG. 4C to limit or prevent foot drop, and position 3 on the medial side of the ankle to limit or prevent eversion.

The direction of force may be changed by the position of the cable guide, and/or the orientation of the proximal cuff. For example, the cuff containing the adjustment mechanism may be able to rotate or be attached in any position on the ankle in order to position the tensioning element on the desired side of the ankle. The device may contain multiple tensioning elements, which can be activated dependently or independently.

Figure 7:
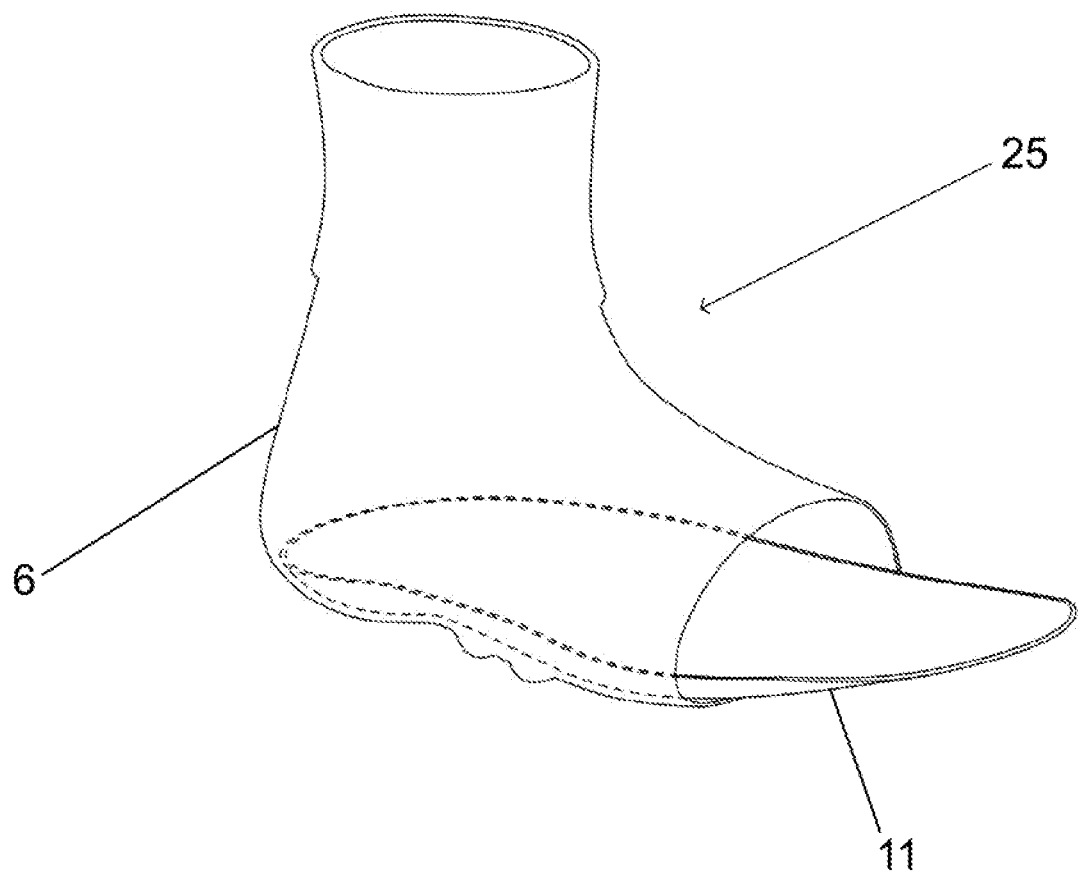
FIG. 7 displays an additional distal portion which may be optionally incorporated into the ankle orthoses containing the sock as described in embodiments 3 and 4.

The embodiment containing the cable guide may incorporate custom or off-the-shelf inserts in order to provide further stability or pressure distribution around any region of the foot or ankle. For example, a custom foot orthotic (11) (as shown in FIG. 7), may be incorporated into the sock. By adding tension to the cable guide (FIG. 4A), force will be applied to the foot orthotic insert (11), which will create a distributed force along the user's foot.

Figure 5A:
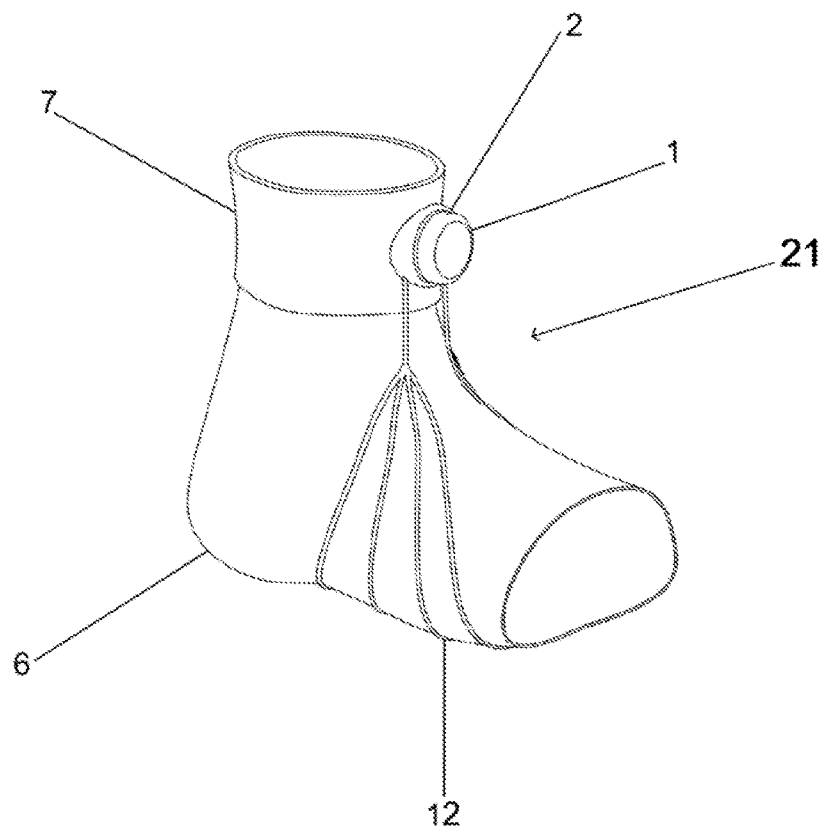
FIGS. 5A and 5B displays a lateral view of the ankle orthosis comprised of a proximal cuff and sock and incorporating a tensioning web as described in embodiment 4.

Preferred Embodiment Four: Multi-Axis Rotation Control Ankle Brace with Tensioning Web In a fourth embodiment, the brace is comprised of a proximal cuff and sock as shown in FIG. 5A. In this embodiment, the tensioning element is comprised of an adjustment mechanism (1) and a tensioning web (12). The tensioning web may be directly connected to the adjustment mechanism, or it may be connected to the adjustment mechanism indirectly by one or more cable (3), similarly to that described in embodiment 1.

Figure 5B:
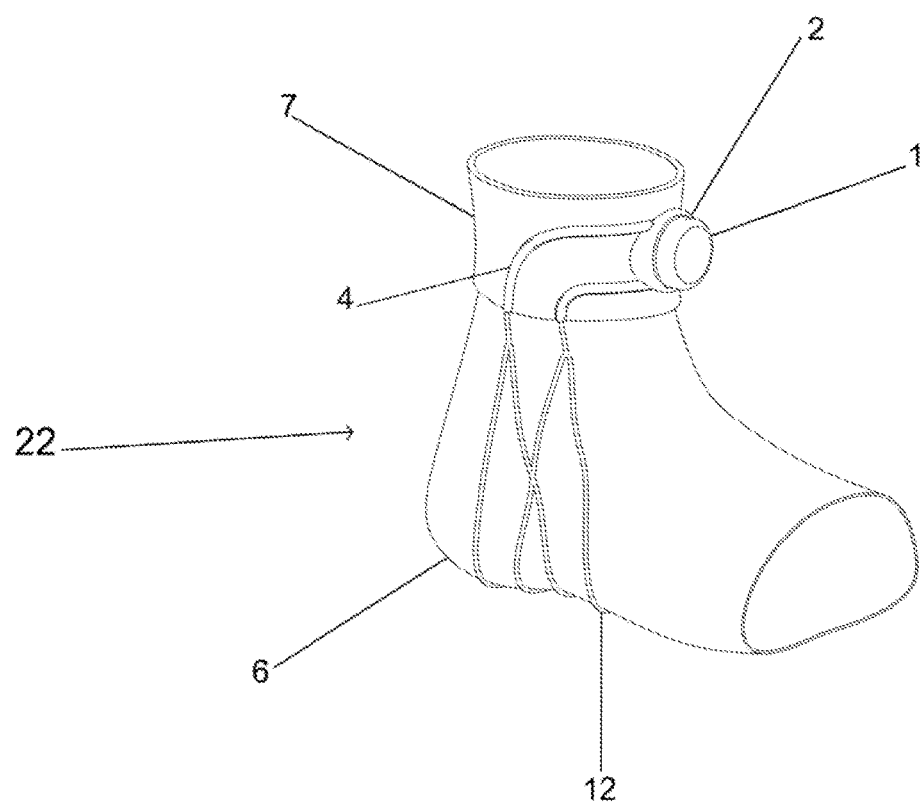

In this embodiment, one or more tensioning web(s) (12) may run along or through the sleeve or sock, for example channels within a fabric. The positioning of the channels guides the direction of force around the joint. As shown in FIG. 5A, the tensioning element(s) may attach directly to an adjustment mechanism, for example a rotary dial, that can increase tension on one or both sides of the foot. In one embodiment (as shown in FIG. 5A), rotation of the dial increases tension equivalently on both sides of the foot. As shown, this would prevent foot drop and also support against both eversion and inversion. Alternatively, the tensioning web can be located on the lateral side of the ankle (as shown in FIG. 5B) to prevent inversion. The dial may increase tension on one side of the foot upon clockwise rotation and decrease tension on the opposite side upon counterclockwise rotation to prevent either inversion or eversion based on the user need. Alternatively, the tension may be disengaged rapidly, e.g. by pulling out or pushing in the dial. The direction of force may be changed based on the positioning of the channels and tensioning elements throughout the sleeve relative to the axes of the ankle. The direction may also be changed by altering the position of channels within the proximal cuff or selecting different channels to feed the tensioning element through, in which the tensioning element is connected to the adjustment mechanism.

Direction and magnitude of force may be customized by the form of the tensioning web itself, including changing the geometry, degree or pattern of branching of the web, the material type, or the material thickness. The tensioning web may be designed to distribute forces in an asymmetric manner or mostly balanced across one or more axes of rotation.

In another embodiment, the sock or sleeve is knitted or stitched or otherwise attached or bonded with materials of different elasticity and or rigidity to allow range of motion in some directions and limit it in others. Regions of the mesh are optionally under static tension which may be optimized for variable directional support. Elastic materials may be weaved together or embedded or attached operationally either inside, outside or within the sock (6). Performance may be adjusted/modified by the geometry, density of mesh, and/or diameter/geometry of the fibers. For example, inversion control may be achieved by having materials of distal elasticity integrated on the lateral side of the sock to restrict rotation in the sagittal plane. Another example is to restrict foot drop and/or promote dorsiflexion plantar flexion by incorporating inelastic mesh in the anterior region of the sleeve while the remaining material remains relatively elastic as to not obstruct normal range of motion in other directions. The device may optionally incorporate a rigid or semi rigid foot orthosis (11), insert, sole or shoe. In some embodiments, the fibers may be directly or indirectly connected to an adjustment mechanism, such as a rotary dial, in order to increase or decrease tension and resulting rigidity of a region of the sock. In others embodiments, the range of motion in a given direction may be controlled statically by the mesh characteristics without required adjustment by the user.

Preferred Embodiment Five: Multi-Axis Rotation Control Ankle Brace with Hinge

Figure 6A:
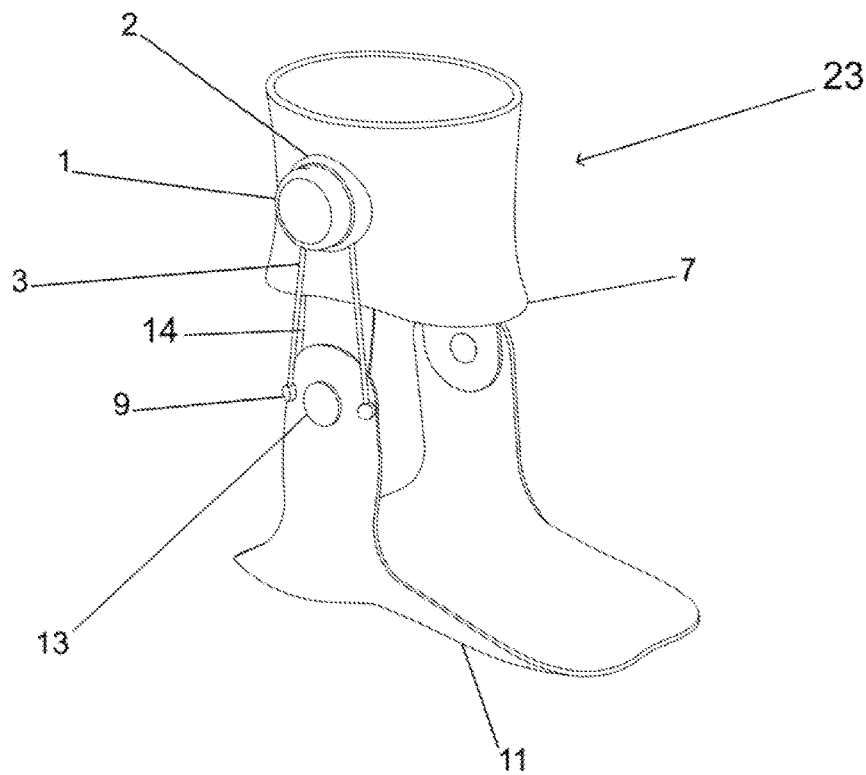
FIG. 6A displays a rotation control ankle orthosis comprised of a proximal cuff and an adjustable tensioning apparatus connected by a hinge, and incorporating an adjustable tensioning mechanism.
Figure 6B:
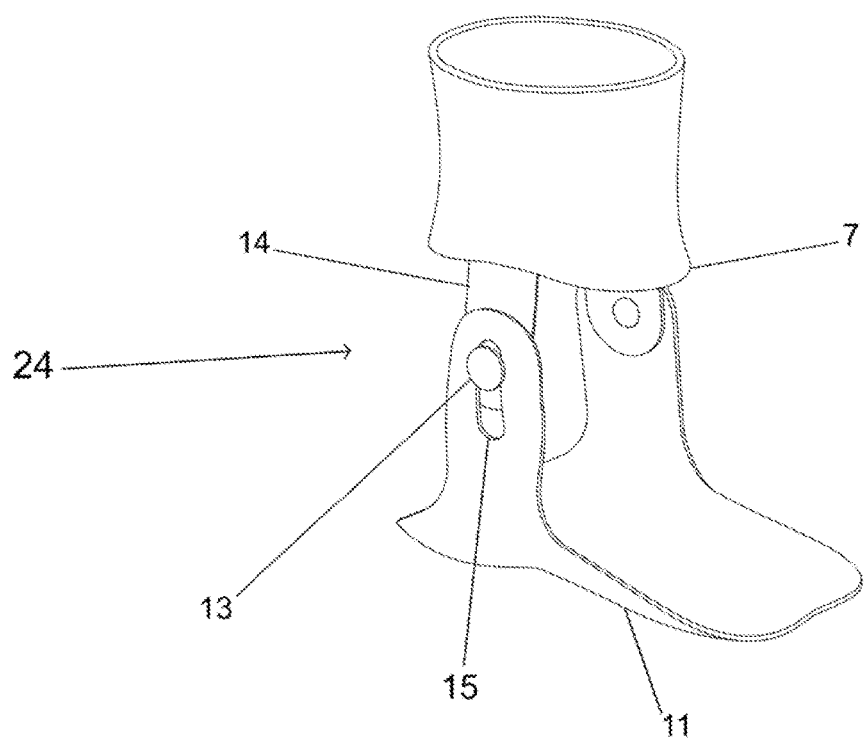
FIG. 6B illustrates an optional slot that may be incorporated into the hinge in FIG. 6B.

In another embodiment, the brace may optionally contain a hinge on the medial and lateral sides of the ankle joint, which allows rotation around the ML axis, but prevents rotation in the AP and vertical axes (as shown in FIG. 6A). The device contains a proximal cuff (3), one or more vertical member (14), one or more hinge (13), and a distal portion (11). The hinge may optionally contain one or more slot (15) on the medial and/or lateral side of the joint (as shown in FIG. 6B). The example in FIG. 6B would allow for movement around the ML axis and limited inversion, with the range of inversion dependent on the size of the slot. Alternatively, a slot located in the medial side of the joint would prevent inversion, but allow a limited range of eversion. It should be understood that the path of the slot can be modified to allow restricted range of motion around the vertical axis, and/or the AP axis. The hinge may be combined with the adjustable tensioning apparatuses described in preferred embodiments 1-4 as explained herein.

In another embodiment, the hinge may incorporate a pulley to which a rigid or semi-rigid tensioning element is connected (FIG. 6A). In this case, the tensioning element is comprised of an adjustment mechanism (1) and a cable (3) connected to the vertical member (14) around the hinge. In this example, rotating the dial counterclockwise would increase tension in the cable anterior to the hinge center while decreasing tension in the cable posterior to the hinge center. The effect would support dorsiflexion, for example to prevent foot drop. The cables may be anchored around the hinge center at any point on the distal portion (11), or they may be connected directly to the hinge (13) to generate a torque around the hinge center.

Embodiments of the invention also include a computer readable medium comprising one or more computer files comprising a set of computer-executable instructions for performing one or more of the calculations, steps, processes, and operations described and/or depicted herein. In exemplary embodiments, the files may be stored contiguously or non-contiguously on the computer-readable medium. Embodiments may include a computer program product comprising the computer files, either in the form of the computer-readable medium comprising the computer files and, optionally, made available to a consumer through packaging, or alternatively made available to a consumer through electronic distribution. As used in the context of this specification, a "computer-readable medium" is a non-transitory computer-readable medium and includes any kind of computer memory such as floppy disks, conventional hard disks, CD-ROM, Flash ROM, non-volatile ROM, electrically erasable programmable read-only memory (EEPROM), and RAM. In exemplary embodiments, the computer readable medium has a set of instructions stored thereon which, when executed by a processor, cause the processor to perform tasks, based on data stored in the electronic database or memory described herein. The processor may implement this process through any of the procedures discussed in this disclosure or through any equivalent procedure.

In other embodiments of the invention, files comprising the set of computer-executable instructions may be stored in computer-readable memory on a single computer or distributed across multiple computers. A skilled artisan will further appreciate, in light of this disclosure, how the invention can be implemented, in addition to software, using hardware or firmware. As such, as used herein, the operations of the invention can be implemented in a system comprising a combination of software, hardware, or firmware.

Embodiments of this disclosure include one or more computers or devices loaded with a set of the computer-executable instructions described herein. The computers or devices may be a general purpose computer, a special-purpose computer, or other programmable data processing apparatus to produce a particular machine, such that the one or more computers or devices are instructed and configured to carry out the calculations, processes, steps, operations, algorithms, statistical methods, formulas, or computational routines of this disclosure. The computer or device performing the specified calculations, processes, steps, operations, algorithms, statistical methods, formulas, or computational routines of this disclosure may comprise at least one processing element such as a central processing unit (i.e., processor) and a form of computer-readable memory which may include random-access memory (RAM) or read-only memory (ROM). The computer-executable instructions can be embedded in computer hardware or stored in the computer-readable memory such that the computer or device may be directed to perform one or more of the calculations, steps, processes and operations depicted and/or described herein.

Additional embodiments of this disclosure comprise a computer system for carrying out the computer-implemented method of this disclosure. The computer system may comprise a processor for executing the computer-executable instructions, one or more electronic databases containing the data or information described herein, an input/output interface or user interface, and a set of instructions (e.g., software) for carrying out the method. The computer system can include a stand-alone computer, such as a desktop computer, a portable computer, such as a tablet, laptop, PDA, or smartphone, or a set of computers connected through a network including a client-server configuration and one or more database servers. The network may use any suitable network protocol, including IP, UDP, or ICMP, and may be any suitable wired or wireless network including any local area network, wide area network, Internet network, telecommunications network, Wi-Fi enabled network, or Bluetooth enabled network. In one embodiment, the computer system comprises a central computer connected to the internet that has the computer-executable instructions stored in memory that is operably connected to an internal electronic database. The central computer may perform the computer-implemented method based on input and commands received from remote computers through the internet. The central computer may effectively serve as a server and the remote computers may serve as client computers such that the server-client relationship is established, and the client computers issue queries or receive output from the server over a network.

The input/output interfaces may include a graphical user interface (GUI) which may be used in conjunction with the computer-executable code and electronic databases. The graphical user interface may allow a user to perform these tasks through the use of text fields, check boxes, pull-downs, command buttons, and the like. A skilled artisan will appreciate how such graphical features may be implemented for performing the tasks of this disclosure. The user interface may optionally be accessible through a computer connected to the internet. In one embodiment, the user interface is accessible by typing in an internet address through an industry standard web browser and logging into a web page. The user interface may then be operated through a remote computer (client computer) accessing the web page and transmitting queries or receiving output from a server through a network connection. In another embodiment, the user interface may be managed and controlled through an App or program on a phone, tablet, or other portable electronic device.

One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all the references cited in this disclosure are each individually incorporated by reference herein in their entireties and as such are intended to provide an efficient way of supplementing the enabling disclosure of this invention as well as provide background detailing the level of ordinary skill in the art.

Methods of Use

The device in embodiments 1-5 are designed to maximize ease of use and comfort for the user. The device is comprised of lightweight, durable materials including fabrics, plastics, elastomers, and 3D printed thermoplastics. In aspects, the user can easily and rapidly (within 10 seconds) don and doff the device. In some embodiments, the proximal cuff and sock may be flexible so that the user can easily stretch the material to slide their foot and ankle into the device. In other embodiments, the device may contain an opening (as shown in FIG. 8), for example made of hook (27) and loop, so that the user can quickly open and close the device to don and doff. The device can be manufactured to have a low profile, in order to fit comfortable and conveniently within the user's footwear. Alternatively, the device may connect to the user's footwear internally or externally. In other embodiments, the device itself may substitute for the user's footwear and function as a shoe with an integrated tensioning mechanism.

In the various embodiments of the present disclosure, the magnitude and direction of force applied (or resistance or tension generated in the brace) can readily be tailored to the user based on their size, weight, joint geometry, injury, and desired activity. Braces as described herein can be lightweight, robust, low-profile, and well-fitting to users. Unlike braces in the prior art, those disclosed herein can be narrow and lightweight to be worn within the shoe, which is required for high-performance athletics but is not enabled by many existing braces on the market.

The various embodiments of the ankle brace of the present disclosure can be used, by way of non-limiting examples: prophylactically to prevent injury; to reduce joint pain (e.g. during physical exercise or athletic competition); to rehabilitate existing injuries; post-operatively (high tension braces to immobilize the joint to a comfortable level within one or more desired range of motion); to assist or augment movement within a desired direction (e.g. in a direction limited by muscle, tendon or ligament deficiency or damage), and to provide stability and alignment to the joint.

The device described in embodiments (16, 17, 18, 20, 21, 22, 23) can correct the position of the foot relative to the user's ankle to restore proper gait, improve user's stability and prevent falls. For example, the user can address foot drop through the method of 1) sliding their foot through the proximal cuff (7), in some embodiments, sliding their foot through the sock (6), 2) optionally adjusting the position of the tensioning mechanism as described in the embodiments (16, 17, 18, 20, 21, 22, 23), which will determine the effective axis of rotation for correction, and 3) adjusting the tension on the device to apply a force around the effective axis of rotation, which will determine the degrees of corrective rotation around that axis. For example, a user with foot drop would don the device, and rotate the dial, by example, one rotation to increase dorsiflexion by 3° around the ML axis, therefore restoring the angle of the foot to normal (e.g. 900 offset from the vertical axis).

In other uses, the user may apply the device in embodiments (16, 17, 18, 20, 21, 22, 23) to limit rotation of the joint within one or more directions. For example, an individual with chronic ankle instability (CAI) leading to frequent inversion, would 1) don the device, for example shown in FIG. 3A, 2) optionally adjust the position of the device using the anchor (9) positioning, and 3) use the adjustment mechanism (1) to apply force on the lateral side of the ankle, therefore limiting rotation about the AP axis and stabilizing the ankle.

In other uses, the user may apply the device in embodiments (16, 17, 18, 20, 21, 22, 23) to augment movement of the joint in one or more directions. For example, an athlete intending to increase plantarflexion force of would use a device similar containing an elastomeric tensioning element on the posterior side of the ankle (aligned with the Achilles tendon). The user would 1) don the device, for example the device shown in FIG. 3A, 2) optionally adjust the position of the device, and 3) increase force in the tensioning element using the adjustment mechanism to resist dorsiflexion but augment plantarflexion. Such an application could increase the force of plantarflexion, for example to increase the strength and speed of a runner.

In other uses, the user may apply the device in embodiments (16, 17, 18, 20, 21, 22, 23) to support recovery or improve range of motion of the muscle, ligament, tendon, cartilage, and/or bone of the foot/ankle post-operation or post-injury. Additionally, the user may use the device to maintain joint function during the recovery period while protecting the joint from further damage. For example, for a user with lateral tendon tear, the user would 1) don the device, for example shown in FIG. 4A, 2) optionally adjust the position of the device, and 3) increase force in the tensioning element using the adjustment mechanism to prevent inversion while allowing range of motion in other axes, therefore protecting the lateral ligaments from further strain.

The embodiments described (16, 17, 18, 20, 21, 22, 23) are capable of unloading a region of the ankle joint based on the direction and magnitude of force generated by the tensioning element. This can be achieved in one aspect by generating a counterforce on one side of the ankle to reduce contact force on the opposite side. For example, by engaging an elastomeric tensioning element on the medial side of the user's ankle, the lateral side of the ankle will be separated. This will separate the lateral side of the ankle, and act as a spring to reduce the force within that region of the joint upon impact with the ground at each step. The mechanism can also reduce forces in an osteoarthritic or damaged region of the joint by altering the user's gait. For example, by engaging the tensioning element to support dorsiflexion, generating a torque around the ML axis of the ankle, the posterior region of the ankle will contact the ground force and experience the initial impact. In this way, the anterior region of the ankle can be shielded from more significant forces that the user would normally experience without use of the device. In the case of an individual with ankle OA in the anterior region of their joint, this would significantly reduce their pain during activity.

The device is designed such that it may remain in the user's footwear after removal, or it may remain attached to the user and removed from the footwear for use without the footwear. In other embodiments, the proximal cuff (7) and/or sock (6) may be opened and closed around the user's foot for attachment (see FIG. 8).

These embodiments may also be equipped with at least one sensor that collects useful information on gait, biomechanics, and health of the joint. This information may then be used to tailor or tune the device more precisely to the needs of the user, or inform a medical professional of information helpful in making decision on a rehabilitation or treatment regimen, including decisions related to surgical procedures and joint implants. The device can also augment the function and performance of the joint post-operatively and compliment the function of an implanted device or component, actively or passively.

It should be understood that the described embodiments are by example only. The same embodiments may incorporate springs or other energy storage elements to generate force across the joint in a similar fashion to the tensioning elements described. Additionally, adjustable compression mechanisms may substitute for the adjustable tensioning mechanisms in order to perform similar functions as described in the multi-axis rotation control brace.

The invention claimed is:

1. An ankle orthosis wearable relative to an ankle and a foot of a wearer, the ankle orthosis comprising:
   a proximal portion affixable above the ankle of the wearer;
   a distal portion extendable below the ankle of the wearer; and
   a tensioning apparatus including an adjustment mechanism and a tensioning element including at least one cable extending outward therefrom, the at least one cable connecting the proximal portion to the distal portion and extending within the distal portion below the ankle of the wearer;
   wherein the adjustment mechanism, via the at last one cable, controls a plurality of forces with respect to more than one axis of rotation of an ankle joint of the wearer.

2. The ankle orthosis of claim 1, wherein the proximal portion and the distal portion of the ankle orthosis are connected by one or more hinges.

3. The ankle orthosis of claim 2, further comprising one or more slots, wherein the one or more slots are optionally contained within at least one side of the hinge.

4. The ankle orthosis of claim 1, further comprising one or more sensors, wherein the one or more sensors collect information on wearer compliance, range of motion, biomechanical alignment and function, stability, relative position, gait, joint health, biometrics, or combinations thereof.

5. The ankle orthosis of claim 4, wherein the information is used to design or modify the ankle orthosis, to effect a function of other external or implantable devices, or to apply or adjust corrective or assistive force or forces across and/or around the ankle joint of the wearer.

6. The ankle orthosis of claim 1, wherein the tensioning element comprising an energy storage element, elastomeric material, elastomer, band, web, webbing, spring, piston, electromagnetic material, or combinations thereof.

7. The ankle orthosis of claim 1, further comprising a tension adjusting mechanism, at least one cable portion, and, optionally, at least one elastomeric band, elastomeric web, or elastomeric material, that can be adjust tensile force or forces along one or more axes.

8. The ankle orthosis of claim 1, further comprising one or more moveable anchor or anchor points, wherein the one or more moveable anchor or anchor points direct the plurality of forces generated by the tensioning element across and/or around the axes of rotation of the ankle joint of the wearer.

9. The ankle orthosis of claim 1, further comprising one or more channels, wherein the one or more channels direct the plurality of forces generated by the tensioning element across and/or around the axes of rotation of the ankle joint of the wearer.

10. The ankle orthosis of claim 1, wherein the proximal portion of the ankle orthosis optionally connects to a knee orthosis and/or a hip orthosis.

11. The ankle orthosis of claim 1, wherein the distal portion of the ankle orthosis optionally connects to and/or integrates with a foot orthotic.

12. The ankle orthosis of claim 1, wherein the adjustment mechanism is motorized, and wherein the plurality of forces generated by the tensioning apparatus are adjusted or changed automatically, partially automatically, or manually.

13. The ankle orthosis of claim 1, wherein a boot, shoe, or other footwear comprise the ankle orthosis or are integrated with the ankle orthosis.

14. The ankle orthosis of claim 1, wherein all or part of the proximal portion and/or the distal portion of the ankle orthosis are connected to or integrated with a shoe, a boot, or other footwear.

15. The ankle orthosis of claim 1, wherein the ankle orthosis is affixed using a rigid material, a semi-rigid material, an inelastic material, an elastic material, or combinations thereof.

16. The ankle orthosis of claim 1, wherein the tensioning element further comprises one or more adjustable springs or one or more elastomeric element, wherein the one or more adjustable springs or the one or more elastomeric element store a compressive force or forces.

17. The ankle orthosis system of claim 1, where the at least one cable and the cable guide extending within the distal portion includes being extendable below the ankle and underneath the foot of the wearer.

18. An ankle orthosis wearable relative to an ankle and a foot of a wearer, the ankle orthosis comprising:
   a proximal cuff affixable above the ankle of the wearer;
   a sock extendable below the ankle of the wearer and encapsulating the foot of the wearer; and
   a tensioning apparatus including an adjustment mechanism and a tensioning element including at least one cable extending outward therefrom, the at least one cable connecting the proximal cuff to the sock;
   wherein the adjustment mechanism via the at least one cable, controls a plurality of forces with respect to more than one axis of rotation of an ankle joint of the wearer.

19. The ankle orthosis of claim 18, wherein the at least one cable is removably attached to one or more different areas of the sock.

20. The ankle orthosis of claim 18, wherein the at least one cable is connected to one or more cable guides.

21. The ankle orthosis of claim 18, wherein the tensioning element comprises an energy storage element, elastomeric material, elastomer, band, web, webbing, spring, piston, electromagnetic material, or combinations thereof.

22. The ankle orthosis of claim 18 wherein the tensioning element is operably attached to one or more preset or predetermined locations on the sock.

23. The ankle orthosis of claim 18, further comprising one or more sensors, wherein the force or forces provided by the tensioning element are automatically adjusted based on information provided by the one or more sensors.

\* \* \* \* \*